United States Patent [19]

Almén et al.

[11] Patent Number: 5,348,954
[45] Date of Patent: Sep. 20, 1994

[54] HETEROCYCLIC CHELATING AGENTS

[75] Inventors: Torsten Almén, Malmö, Sweden; Arne Berg, Blommenholm, Norway; Harald Dugstad; Jo Klaveness, both of Oslo, Norway; Klaus D. Krautwurst, Stabekk; Pal Rongved, Hellvik, both of Norway

[73] Assignee: Nycomed Imaging AS, Oslo, Norway

[21] Appl. No.: 690,975

[22] PCT Filed: Jan. 15, 1990

[86] PCT No.: PCT/EP90/00079

§ 371 Date: Jul. 24, 1991

§ 102(e) Date: Jul. 24, 1991

[87] PCT Pub. No.: WO90/08138

PCT Pub. Date: Jul. 26, 1990

[30] Foreign Application Priority Data

Jan. 13, 1989 [GB] United Kingdom ............... 8900719

[51] Int. Cl.$^5$ .................. A61K 31/15; C07D 211/08; C07D 241/04; C07D 279/12; C07D 265/30
[52] U.S. Cl. .................. 514/227.5; 514/227; 514/231.5; 514/231.8; 514/235.5; 514/236; 514/252; 514/255; 514/316; 514/326; 514/327; 514/331; 514/422; 514/425; 544/58.1; 544/58.6; 544/86; 544/106; 544/130; 544/141; 544/162; 544/221; 544/306; 544/360; 544/399; 546/188; 546/190; 546/208; 548/556
[58] Field of Search ............... 424/1.1; 534/10; 544/2, 544/4, 7, 64, 224, 225, 106, 162, 58.6, 58.1, 221, 86, 130, 306, 399, 360, 141; 514/231.2, 231.5, 231.8, 237.8, 227.5, 227.8, 235.5, 235.8, 252, 255, 316; 546/188, 190, 208; 548/556

[56] References Cited

U.S. PATENT DOCUMENTS

| | | | |
|---|---|---|---|
| 2,387,735 | 10/1945 | Bersworth | 260/534 |
| 2,407,645 | 9/1946 | Bersworth | 260/534 |
| 4,639,365 | 1/1987 | Sherry | 424/9 |
| 5,130,437 | 7/1992 | Rocklage et al. | 546/261 |

FOREIGN PATENT DOCUMENTS 0071564 2/1983 European Pat. Off.
0130934 6/1984 European Pat. Off.
(List continued on next page.)

OTHER PUBLICATIONS

Krejcarek et al., *Biochemical and Biophysical Research Communications*, 77, 581–585, 1977.

Hnatowich et al., *Science*, 220, 613–615, 1983.
Meares et al., *Analytical Biochemistry*, 142, 68–78, 1984.

Primary Examiner—Robert L. Stoll
Assistant Examiner—Lara E. Chapman
Attorney, Agent, or Firm—Bacon & Thomas

[57] ABSTRACT

Heterocylic chelating agents and salts thereof of formula I:

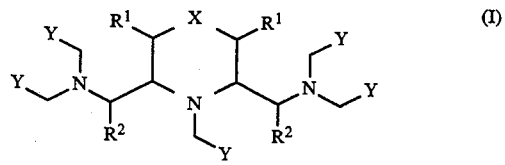

wherein X represents a bond, O or S, or a group $CHR^1$ or $NR^3$;

$R^1$ represents H, a group $OR^3$ or $NR^3R^3$, or an alkyl or alkoxyalkyl group optionally substituted by a hydroxyl group or by a group $NR^3R^3$ or $CON^3R^3$;

each $R^2$ represents H, or an alkyl or alkoxy group optionally substituted by a hydroxyl or alkoxy group;

each $R^3$ represents H, an optionally hydroxylated alkyl group or a group $CH_2Y$;

Y represents a group COZ, CON(OH)$R^4$, POZ$_2$ or SO$_2$Z;

Z represents a group $OR^4$, $NR^4R^4$ or

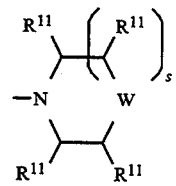

where each $R^{11}$ is H, a hydroxyl group or an optionally hydroxylated alkyl group, s is 0, 1 or 2, and W is $CHR^{11}$, $NR^{11}$ or an oxygen atom; and each $R^4$ represents H, or an optionally mono- or polyhydroxylated alkyl, alkoxyalkyl or polyalkoxyalkyl group;

with the provisos that where s is 0 then W is $CHR^{11}$ and that where X represents a bond or $CHR^1$, at least one group $R^1$ or $R^2$ represents other than H or an unsubstituted alkyl group. A process for preparing these agents and methods of heavy metal detoxification using these agents are also described.

8 Claims, No Drawings

FOREIGN PATENT DOCUMENTS

| | | |
|---|---|---|
| 0250358 | 6/1987 | European Pat. Off. . |
| 0263059 | 9/1987 | European Pat. Off. . |
| 0258616 | 3/1988 | European Pat. Off. . |
| 0299795 | 7/1988 | European Pat. Off. . |
| 0277088 | 8/1988 | European Pat. Off. . |
| 0165728 | 12/1988 | European Pat. Off. . |
| 0331616 | 9/1989 | European Pat. Off. . |
| 2918842A1 | 12/1979 | Fed. Rep. of Germany . |
| 3401052A1 | 7/1984 | Fed. Rep. of Germany . |
| 3633243A1 | 3/1988 | Fed. Rep. of Germany . |
| 3633245A1 | 3/1988 | Fed. Rep. of Germany . |
| 3640708A1 | 6/1988 | Fed. Rep. of Germany . |
| WO89/06979 | 8/1989 | PCT Int'l Appl. . |

HETEROCYCLIC CHELATING AGENTS

This application is the U.S. national phase of International Application No. PCT/EP90/00079, filed Jan. 15, 1990.

The present invention relates to certain novel chelating agents, in particular heterocyclic polyamines, and to their uses, especially their medical uses.

The medical use of chelating agents is well established, for example as stabilizers for pharmaceutical preparations, as antidotes for poisonous heavy metal species and as diagnostic agents for the administration of metal species (e.g. ions or atoms) for diagnostic techniques such as X-ray, magnetic resonance imaging (MRI) or ultrasound imaging or scintigraphy.

Polyamine chelating agents, for example aminopoly(carboxylic acid or carboxylic acid derivative) (hereinafter APCA) chelating agents and their metal chelates, are well known and are described for example in U.S. Pat. No. 2,407,645 (Bersworth), U.S. Pat. No. 2,387,735 (Bersworth), EP-A-71564 (Schering), EP-A-130934 (Schering), EP-A-165728 (Nycomed AS), DE-A-2918842 (Rexolin Chemicals AB), DE-A-3401052 (Schering), EP-A-258616 (Salutar), DE-A-3633245 (Schering), EP-A-263059 (Schering), EP-A-277088 (Schering) and DE-A-3633243 (IDF).

Thus, for example, EP-A-71564 describes paramagnetic metal chelates, for which the chelating agent is nitrilotriacetic acid (NTA), N,N,N',N'-ethylenediamine-tetraacetic acid (EDTA), N-hydroxyethyl-N,N',N'-ethylenediamine-triacetic acid (HEDTA), N,N,N',N'',N''-diethylenetriamine-pentaacetic acid (DTPA) and N-hydroxyethylimino-diacetic acid, as being suitable as contrast agents for MRI, contrast being achieved by the effect of the magnetic field of the paramagnetic species (e.g. Gd (III)) with the chelating agents serving to reduce the toxicity and to assist administration of that paramagnetic species.

Amongst the particular metal chelates disclosed by EP-A-71564 was Gd DTPA, the use of which as an MRI contrast agent has recently received much attention. The Gd(III) chelate of 1,4,7,10-tetraazacyclododecanetetraacetic acid (DOTA), referred to in DE-A-3401052 (Schering) and in U.S. Pat. No. 4,639,365 (University of Texas), has also recently received attention in this regard.

To improve stability, water solubility and selectivity, relative to the APCA chelating agents described in EP-A-71564, Schering, in EP-A-130934, have proposed the partial substitution for the N-attached carboxyalkyl groups of alkyl, alkoxyalkyl, alkoxycarbonylalkyl or alkylaminocarbonylalkyl groups, where any amide nitrogens may themselves carry polyhydroxyalkyl groups. More recently, to improve compatibility, stability, solubility and selectivity, in EP-A-250358 Schering have proposed a narrow range of compounds having a DTPA-like structure including a bridging alkylene chain. Thus EP-A-250358 specifically discloses several 2,6-bis-aminomethyl-1-piperidine compounds.

However, all hitherto known APCA chelating agents and their metal chelates encounter problems of toxicity, stability or selectivity and there is thus a general and continuing need for such polyamine chelating agents which form metal chelates of reduced toxicity, improved stability or improved water solubility.

Nycomed, in European Patent Application No. EP-A-299795 suggest that the toxicity of certain APCA chelating agents and their chelates may be reduced by introducing at least one hydrophilic moiety as a substituent on one or more of the alkylene bridges between the amine nitrogens.

We now propose a novel class of polyamine chelating agents which incorporate within their structure a 5- or 6-membered saturated heterocyclic ring and carry hydrophilic moieties on or in the ring or on the alkylene bridges between the amine nitrogens.

Thus viewed from one aspect the present invention provides a compound of formula I

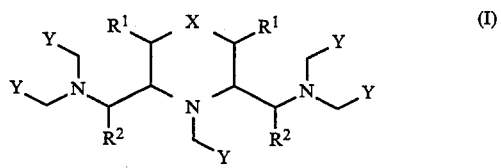

(wherein X represents a bond, an oxygen or sulphur atom or a group of formula $CHR^1$ or $NR^3$;

each $R^1$ which may be the same or different represents a hydrogen atom, a group of formula $OR^3$ or $NR^3R^3$ or a $C_{1-8}$alkyl or $(C_{1-8}alkoxy)$-$C_{1-8}$alkyl group optionally substituted by a hydroxyl group or by a group of formula $NR^3R^3$ or $CONR^3R^3$;

each $R^2$ which may be the same or different represents a hydrogen atom or a $C_{1-8}$alkyl or $C_{1-8}$alkoxy group optionally mono- or poly- substituted by hydroxyl or $C_{1-8}$alkoxy groups;

each $R^3$ which may be the same or different represents a hydrogen atom, an optionally mono- poly-hydroxylated $C_{1-8}$alkyl group or a group of formula $CH_2Y$;

Y represents a group of formula $COZ$, $CON(OH)R^4$, $POZ_2$ or $SO_2Z$; and

Z represents a group of formula $OR^4$, $NR^4R^4$

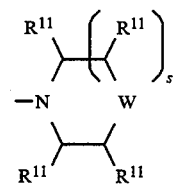

where each $R^{11}$ which may the same or different is a hydrogen atom, a hydroxyl group or an optionally hydroxylated $C_{1-8}$alkyl group, s is 0, 1 or 2, and W is a group $CHR^{11}$, $NR^{11}$ or an oxygen atom; and each $R^4$ which may be the same or different represents a hydrogen atom or an optionally mono- or polyhydroxylated $C_{1-8}$alkyl, $(C_{1-8}alkoxy)$-$C_{1-8}$alkyl or poly($C_{1-8}$ alkoxy)$C_{1-8}$alkyl group; with the provisos that where s is 0 then in the resultant 5 membered heterocyclic ring W is a $CHR^{11}$ group and that where X represents a bond or a group $CHR^1$ at least one group $R^1$ or $R^2$ represents other than a hydrogen atom or an unsubstitued $C_{1-8}$ alkyl group) or a chelate complex or salt thereof.

Thus, for example, in the compounds of formula I, Z may represent a group of formula $OR^4$ or $NR^4_2$ and each $R^4$ which may be the same or different may represent a hydrogen atom or an optionally hydroxylated alkyl group.

In the compounds of the invention, alkyl or alkylene moieties in groups $R^1$ to $R^4$ and $R^{11}$, unless otherwise stated, may be straight chained or branched and preferably contain from 1 to 6 and most preferably 1 to 4, carbon atoms. Where substituents may themselves optionally be substituted by hydroxyl or alkoxy groups, this may be monosubstitution or polysubstitution and in the case of polysubstitution alkoxy or hydroxyl substituents may be carried by alkoxy substituents.

Where the compounds of the invention incorporate one or more hydrophilic $R^1$ or $R^2$ groups, these are preferably straight-chained or branched moieties having a carbon atom content of from 1 to 8, especially preferably 1 to 6, carbon atoms. The hydrophilic groups may be alkoxy, polyalkoxy, hydroxyalkoxy, hydroxypolyalkoxy, polyhydroxyalkoxy, polyhydroxylated polyalkoxy, hydroxyalkyl, polyhydroxyalkyl, alkoxyalkyl, polyalkoxyalkyl, hydroxylated alkoxyalkyl, polyhydroxylated alkoxyalkyl, hydroxylated polyalkoxyalkyl, or polyhydroxylated polyalkoxyalkyl groups. More preferably however they will be monohydroxyalkyl or polyhydroxyalkyl groups. The hydrophilic groups serve to increase the hydrophilicity and reduce the lipophilicity of the metal chelates formed with the chelating agents of the invention and it is preferred that the compounds of formula I should contain at least 1, conveniently from 1 to 4, and preferably 1, 2 or 3 hydrophilic $R^1$ or $R^2$ groups. As hydrophilic groups, the compounds of the invention may thus include for example hydroxymethyl, 2-hydroxyethyl, 1,2-dihydroxyethyl, 3-hydroxypropyl, 2,3-dihydroxypropyl, 2,3,4-trihydroxybutyl, 1-(hydroxymethyl)-2-hydroxyethyl, methoxymethyl, ethoxymethyl, 2-hydroxyethoxymethyl, methoxyethoxymethyl, (2-hydroxy-ethoxy)ethyl, etc, groups.

Where a group Z in a compound according to the invention is a nitrogen attached heterocyclic ring, it particularly preferably is of formula

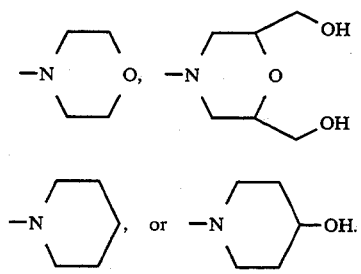

In the compounds of formula I, the groups Y preferably represent carboxylic acid or amide groups, for example groups of formula COOH, CONH$_2$,

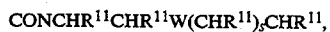

CONHR$^{4''}$ or CONR$^{4''}_2$ (where R$^{4''}$ is an alkyl or mono or poly hydroxyalkyl group, for example a C$_{1-6}$ alkyl group optionally carrying 1, 2, 3 or 4 hydroxyl groups). Particularly preferably, the terminal amine nitrogens, i.e. those carrying two CH$_2$Y groups, will carry a CH$_2$Y group in which Y is an amide group. Where Y is a carboxyl group, the compounds of formula I can conveniently form salts or chelates in which Y represents —COOM (wherein M$^+$ is a monovalent cation or a fraction of a polyvalent cation, for example an ammonium or substituted ammonium ion or a metal ion, for example an alkali metal or alkaline earth metal ion). Particularly preferably, M$^+$ is a cation deriving from an organic base, for example meglumine or lysine. In such salts or chelates one or more (but not necessarily all) of the carboxyl groups are transformed into COOM groups.

It is particularly preferred that the number of the ion-forming groups Y in the compounds of formula I be chosen to equal the valency of the metal species to be chelated by the compound formula I. Thus, for example, where Gd (III) is to be chelated, the compound of formula I (or salt thereof) preferably contains three ion-forming Y groups, for example —COOH (or —COOM). In this way, the metal chelate will be formed as a neutral species, a form preferred since the osmotic pressures in concentrated solutions of such compounds are low and since their toxicities relative to their ionic analogues are significantly reduced.

Compounds of formula I in which all the Y groups carboxyl are —COOH groups or salts or amides of such compounds are especially preferred since compositions containing metal chelates of such compounds can readily be sterilized, for example by autoclaving.

Included amongst the particularly preferred compounds according to the invention are those of formula I wherein R$^1$ represents a hydrogen atom, a hydroxyl group or a hydroxylated alkyl group, R$^2$ represents a hydrogen atom or a hydroxylated alkyl group, R$^3$ represents a hydrogen atom or a group of formula CH$_2$Y, X represents a bond, an oxygen atom, an optionally hydroxylated methylene group or a group NR$^3$, Y represents a group of formula COZ and Z represents a hydroxyl group or a group NHR$^4$, (where R$^{4'}$ represents a hydrogen atom or an optionally hydroxylated alkyl group) and metal chelates and salt thereof.

Especially preferred compounds according to the invention include those of the following formulae:

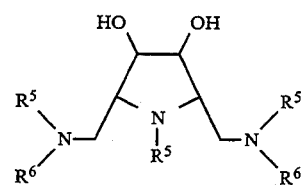
(Ia)

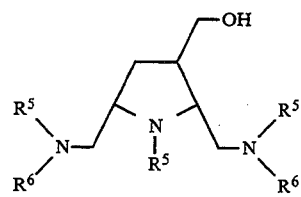
(Ib)

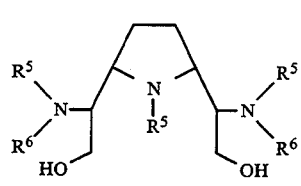
(Ic)

-continued

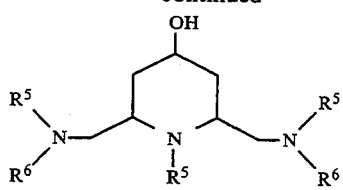 (Id)

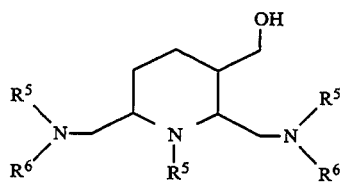 (Ie)

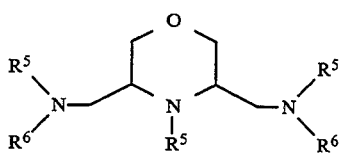 (If)

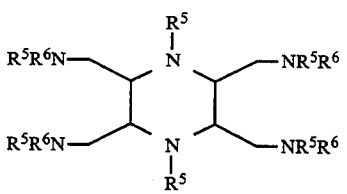 (Ig)

(where $R^5$ represents $CH_2COOH$, $R^6$ represents $CH_2COOH$, $CH_2CON(CH_3)CH_2CHOHCH_2OH$, or $CH_2CONHR^7$ and $R^7$ represents $CH_3$, $CH_2CHOHCH_2OH$ or $CH(CH_2OH)_2$, or $NR^5R^6$ represents a group

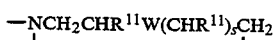

where W represents an oxygen atom or a group $CH_2$ or CHOH, s is 0 or 1 and $R^{11}$ is hydrogen or where s is 1 and W is oxygen each $R^{11}$ may also represent a $C_{1-4}$ hydroxyalkyl group) and the metal chelates and the salts thereof.

Particularly preferred compounds according to the invention include those of formulae:

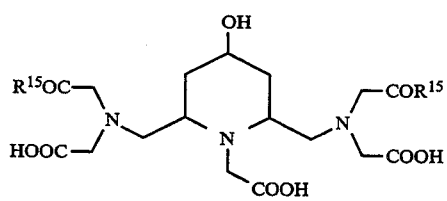 (Ih)

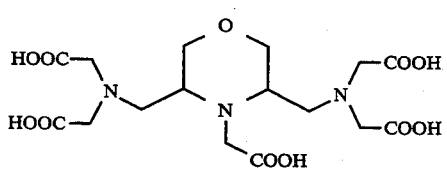 (Ij)

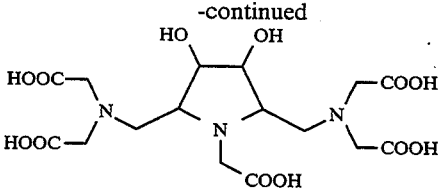 (Ik)

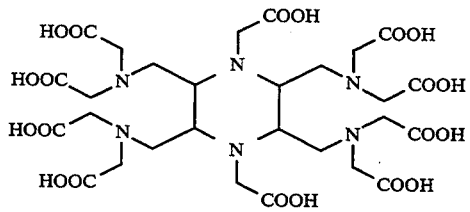 (Il)

(where $R^{15}$ is $NHCH_3$ or $N(CH_2)CH_2CHOHCH_2OH$) and the chelates, e.g. with $Gd^{3+}$ and salts thereof.

Viewed from a further aspect, the invention also provides a process for the preparation of the compounds of the invention, said process comprising one or more of the following steps:

a) reacting a compound of formula II

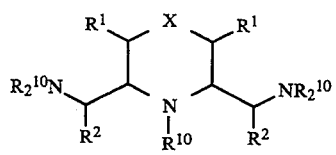 (II)

(wherein X, $R^1$ and $R^2$ are as hereinbefore defined and $R^{10}$ represents a hydrogen atom or a group $CH_2Y$ where Y is as hereinbefore defined, with the proviso that at least one hydrogen is nitrogen-attached) with a compound serving to replace a nitrogen attached hydrogen by a group $CH_2Y$, e.g. a compound of formula III $$L-CH_2-Y \qquad (III)$$

(where L is a nucleophilic leaving group, e.g. a halogen atom, such as chlorine, bromine or iodine); and b) converting a compound of formula I into a chelate complex or salt thereof.

The compounds of formula II may be prepared from unsaturated starting compounds of formula IV

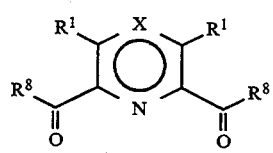 (IV)

(wherein $R^8$ represents a hydroxyl group or a group of formula $NR^9_2$ and each $R^9$ which may be the same or different represents a hydrogen atom or an optionally hydroxylated alkyl group) by i) catalytic reduction of the heterocyclic ring, ii) (where required) amide formation, and iii) reduction of amide functions to amines (optionally involving substituting the carbon of the carboxyl groups shown in formula II with groups $R^2$). These process stages need not be performed in this order.

The following schemes for the preparation of compounds of formula I are provided by way of illustration:

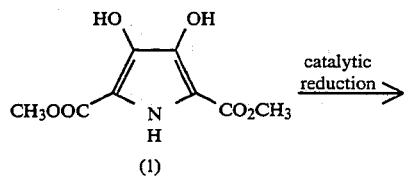
(1)

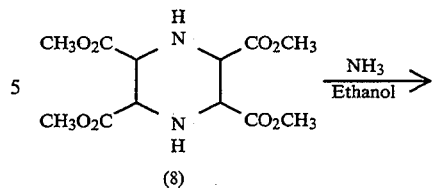
(8)

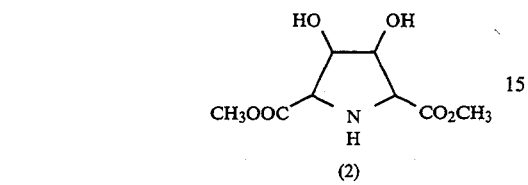
(2)

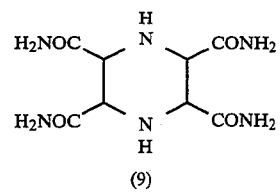
(9)

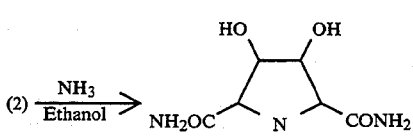
(3)

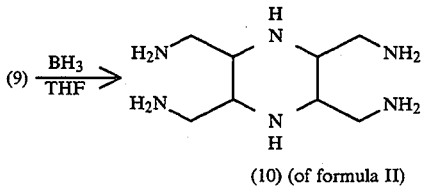
(10) (of formula II)

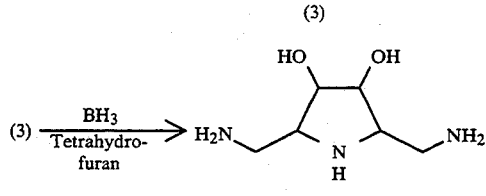
(4) (of formula II)

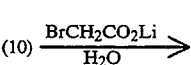

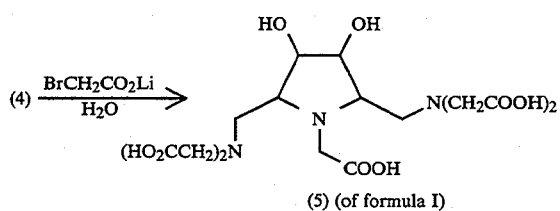
(5) (of formula I)

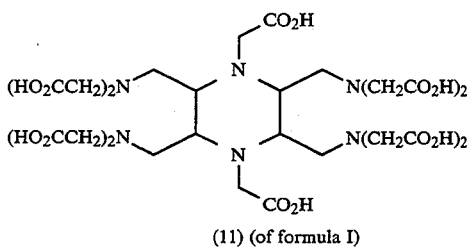
(11) (of formula I)

The starting compound (1) is described by Wahlstroem in Arkiv Kemi 11 (1957)251. Catalytic reduction amidation, reduction and alkylation yields the compound (5) which is a compound according to the invention.

The starting compound (8) is described by Williams et al. in J. Org. Chem. 37 (1972)2963. Amidation, reduction and alkylation yields compound (11) which is a compound according to the invention.

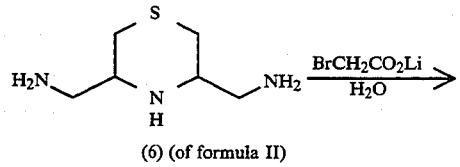
(6) (of formula II)

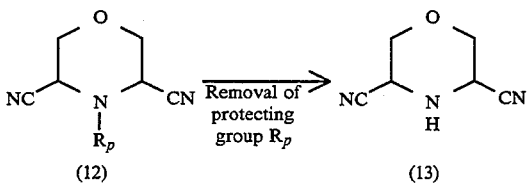
(12)                (13)

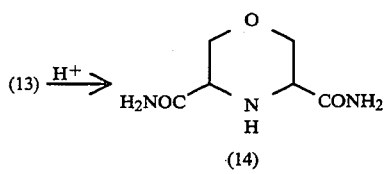
(14)

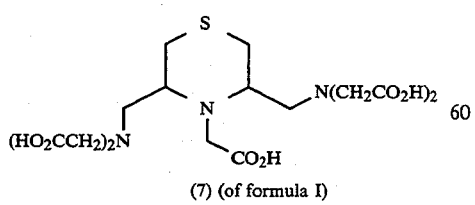
(7) (of formula I)

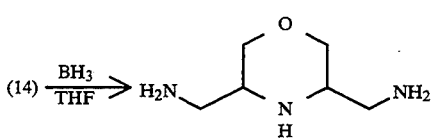
(15) (of formula II)

The starting compound (6) is described by Eremev in Zh. Org. Chim. 21 (1985)2239. Alkylation yields compound (7) which is a compound according to the invention.

(15) $\xrightarrow{\text{BrCH}_2\text{CO}_2\text{Li}}{\text{H}_2\text{O}}$

-continued

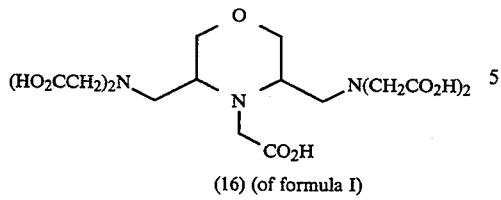
(16) (of formula I)

The starting compound (12) may be prepared analogously to compounds described by Acton et al. in J.Med. Chem. 27 (1984)638. Deprotection, hydrolysis, reduction and alkylation yields compound (16) which is a compound according to the invention.

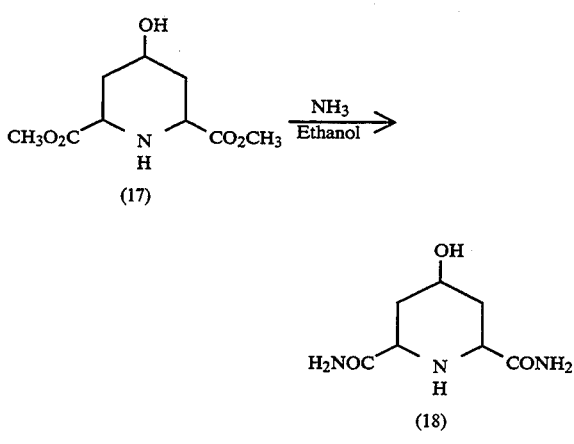

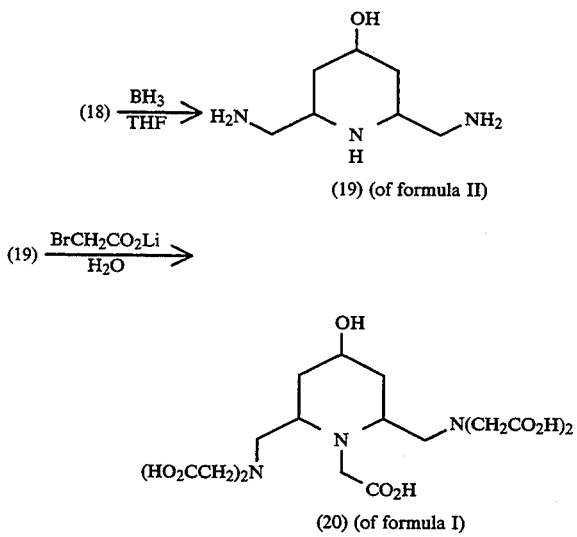
(20) (of formula I)

The starting compound (17) is described by Hermann et al. in Helv. Chim. Acta 59 (1976) 626. Amidation, reduction and alkylation yields compound (20) which is a compound according to the invention.

The introduction of a CH$_2$Y moiety other than an acetic acid residue may for example be Performed as follows:

a) To introduce a phosphonic acid moiety, the general method for synthesis of alpha-aminophosphonic acids described by K. Moedritzer et al. in J. Org. Chem 31 (1966) 1603 may be used.

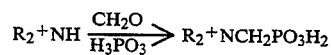

(21)                (22)
(of formula II)     (of formula I)

(where R$^+$$_2$NCH$_2$Y is a compound of formula I).

b) To introduce a hydroxamic acid moiety, the general method for transformation of an activated acid derivative into hydroxamic acid described by P. N. Turowski et al. in Inorg. Chem. 27 (1988) 474 may be used.

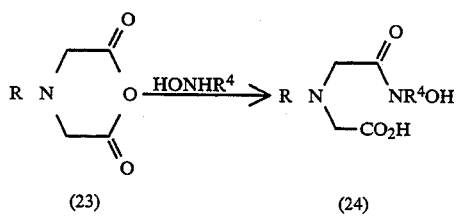

(23)                (24)

(where RN(CH$_2$COOH)CH$_2$Y is a compound of formula I).

c) To introduce a sulfonic acid moiety, synthesis may be performed by alkylation of an amino function for example with iodomethanesulfonic acid

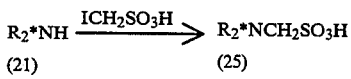

(21)                (25)

(where R*$_2$NCH$_2$SO$_3$H is a compound of formula I).

As mentioned above, the starting materials for the preparation of compounds of formula II may conveniently be unsaturated, e.g. aromatic, heterocycles. Procedures for the catalytic reduction of aromatic heterocycles are described by Nishiki et al. in Tetrahedron Letters 23 (1982) 193 and by Kaiser in J.Org. Chem. 49 (1984) 4203 and elsewhere.

Conversion of hydroxyl groups to groups R$^3$ or R$^4$ can be by conventional methods, e.g. by alkylation.

Amide derivatives of formula I may be produced from the oligo acids by methods analogous to those of EP-A-250358 or of EP-A-299795.

Compounds of formula I wherein Y is a phosphonic acid group may be synthesized by reacting the amines of formula II with formaldehyde/phosphorous acid, e.g. as described by Moedriter in J.Org.Chem. 31 (1966) 1603. Similarly compounds of formula I, wherein Y is a hydroxamic or sulphonic acid group, can be synthesized as described by Turowski et al. in Inorg. Chem. 27 (1988) 474 or by amine reduction using iodomethanesulphonic acid.

Chelants of formula I may be used as the basis for bifunctional chelants or :For polychelant compounds, that is compounds containing several independant chelant groups, by substituting for one Y or R$^1$ or R$^2$ group a bond or linkage to a macromolecule or polymer, e.g. a tissue specific biomolecule or a backbone polymer such as polylysine or polyethyleneimine which may carry several chelant groups and may itself be attached to a macromolecule to produce a bifunctional-polychelant. Such macromolecular derivatives of the compounds of formula I and the metal chelates and salts thereof form a further aspect of the present invention.

The linkage of a compound of formula I to a macromolecule or backbone polymer may be effected by any of the conventional methods such as the mixed anhydride procedure of Krejcarek et al. (see Biochemical and Biophysical Research Communications 77:581 (1977)), the cyclic anhydride method of Hnatowich et al. (see Science 220: 613 (1983) and elsewhere), the backbone conjugation techniques of Meares et al. (see Anal. Biochem. 142: 68 (1984) and elsewhere) and Schering (see EP-A-331616 for example) and by the use of linker molecules as described for example by Nycomed in WO-A-89/06979.

Salt and chelate formation may be performed in a conventional manner.

The chelating agents of the present invention are particularly suitable for use in detoxification or in the formation of metal chelates, chelates which may be used for example in or as contrast agents for in vivo or in vitro magnetic resonance (MR), X-ray or ultrasound diagnostics (e.g. MR imaging and MR spectroscopy), or scintigraphy or in or as therapeutic agents for radiotherapy, and such metal chelates form a further aspect of the present invention.

Salts or chelate complexes of the compounds of the invention containing a heavy metal atom or ion are particularly useful in diagnostic imaging or therapy. Especially preferred are salts or complexes with metals of atomic numbers 20–32,42–44 49 and 57 to 83.

For use as an MR-diagnostics contrast agent, the chelated metal species is particularly suitably a paramagnetic species, the metal conveniently being a transition metal or a lanthanide, preferably having an atomic number of 21–29, 42, 44 or 57–71. Metal chelates in which the metal species is Eu, Gd, Dy, Ho, Cr, Mn or Fe are especially preferred and $Gd^{3+}$, $Mn^{2+}$ and $Dy^{3+}$ are particularly preferred. For such use, the paramagnetic metal species is conveniently non-radioactive as radioactivity is a characteristic which is neither required nor desirable for MR-diagnostics contrast agents. For use as X-ray or ultrasound contrast agents, the chelated metal species is preferably a heavy metal species, for example a non-radioactive metal with an atomic number greater than 37, preferably greater than 50, e.g. $Dy^{3+}$.

For use in scintigraphy and radiotherapy, the chelated metal species must of course be radioactive and any conventional complexable radioactive metal isotope, such as $^{99m}Tc$ or $^{111}In$ for example, may be used. For radiography, the chelating agent may be in the form of a metal chelate with for example $^{67}Cu$.

For use in detoxification of heavy metals, the chelating agent must be in salt form with a physiologically acceptable counterion, e.g. sodium, calcium, ammonium, zinc or meglumine, e.g. as the sodium salt of the chelate of the compound of formula T with zinc or calcium.

Where the metal chelate carries an overall charge, such as is the case with the prior art Gd DTPA, it will conveniently be used in the form of a salt with a physiologically acceptable counterion, for example an ammonium, substituted ammonium, alkali metal or alkaline earth metal cation or an anion deriving from an inorganic or organic acid. In this regard, meglumine salts are particularly preferred.

Viewed from a further aspect, the present invention provides a diagnostic or therapeutic agent comprising a metal chelate, whereof the chelating entity is the residue of a compound according to the present invention, together with at least one pharmaceutical or veterinary carrier or excipient, or adapted for formulation therewith or for inclusion in a pharmaceutical formulation for human or veterinary use.

Viewed from another aspect, the present invention provides a detoxification agent comprising a chelating agent according to the invention in the form of a weak complex or salt with a physiologically acceptable counterion, together with at least one pharmaceutical or veterinary carrier or excipient, or adapted for formulation therewith or for inclusion in a pharmaceutical formulation for human or veterinary use.

The diagnostic and therapeutic agents of the present invention may be formulated with conventional pharmaceutical or veterinary formulation aids, for example stablizers, antioxidants, osmolality adjusting agents, buffers, pH adjusting agents, etc. and may be in a form suitable for parenteral or enteral administration, for example injection or infusion or administration directly into a body cavity having an external escape duct, for example the gastrointestinal tract, the bladder or the uterus. Thus the agent of the present invention may be in a conventional pharmaceutical administration form such as a tablet, capsule, powder, solution, suspension, dispersion, syrup, suppository, etc; however, solutions, suspensions and dispersions in physiologically acceptable carrier media, for example water for injections, will generally be preferred.

Where the agent is formulated for parenteral administration, the carrier medium incorporating the chelate or the chelating agent salt is preferably isotonic or somewhat hypertonic.

Where the diagnostic or therapeutic agent comprises a chelate or salt of a toxic metal species, e.g. a heavy metal ion, it may be desirable to include within the formulation a slight excess of the chelating agent, e.g. as discussed by Schering in DE-A-3640708, or more preferably a slight excess of the calcium salt of such a chelating agent.

For MR-diagnostic examination, the diagnostic agent of the present invention, if in solution, suspension or dispersion form, will generally contain the metal chelate at concentration in the range 1 micromole to 1.5 mole per liter, preferably 0.1 to 700 mM. The diagnostic agent may however be supplied in a more concentrated form for dilution prior to administration. The diagnostic agent of the invention may conveniently be administered in amounts of from $10^{-3}$ to 3 mmol of the metal species per kilogram of body weight, e.g. about 1 mmol Dy/kg bodyweight.

For X-ray examination, the dose of the contrast agent should generally be higher and for scintigraphic examination the dose should generally be lower than for MR examination. For radiotherapy and detoxification, conventional dosages may be used.

Viewed from a further aspect, the present invention provides a method of generating enhanced images of the human or non-human animal body, which method comprises administering to said body a diagnostic agent according to the present invention and generating an X-ray, MR-diagnostics, ultrasound or scintigraphic image of at least a part thereof.

Viewed from a further aspect, the present invention provides a method of radiotherapy practised on the human or non-human animal body, which method comprises administering to said body a chelate of a radioactive metal species with a chelating agent according to the invention.

Viewed from a further aspect, the present invention provides a method of heavy metal detoxification practised on the human or non-human animal body, which method comprises administering to said body a chelating agent according to the invention in the form of a weak complex or salt with a physiologically acceptable counter ion.

Viewed from a yet further aspect, the present invention also provides the use of the compounds, especially the metal chelates, according to the invention for the manufacture of diagnostic or therapeutic agents for use in methods of image generation, detoxification or radiotherapy practised on the human or non-human animal body.

Viewed from a still further aspect, the present invention provides a process for the preparation of the metal chelates of the invention which process comprises admixing in a solvent a compound of formula I or a salt (e.g. the sodium salt) or chelate thereof together with an at least sparingly soluble compound of said metal, for example a chloride, oxide or carbonate.

Viewed from a yet still further aspect, the present invention provides a process for the preparation of the diagnostic or therapeutic agent of the present invention, which comprises admixing a metal chelate according to the invention, or a physiologically acceptable salt thereof, together with at least one pharmaceutical or veterinary carrier or excipient.

Viewed from a yet still further aspect, the present invention provides a process for the preparation of the detoxification agent of the invention, which comprises admixing a chelating agent according to the invention in the form of a salt with a physiologically acceptable counterion together with at least one pharmaceutical or veterinary carrier or excipient.

The disclosures of all of the documents mentioned herein are incorporated by reference.

The present invention will now be illustrated further by the following non-limiting examples. All ratios and percentages given herein are by weight and all temperatures are in degrees Celsius unless otherwise indicated.

EXAMPLE 1

2,6-Bis-aminomethyl-4-hydroxy-N,N',N''-pentakiscarboxymethyl-piperidine

(a) Chelidamic acid-diethylester

Chelidamic acid (25g, 0.136 tool) and 500 ml of ethanol were refluxed while dry hydrogen chloride was bubbled through the suspension. The resultant clear solution was concentrated in vacuo and crystallised from water to give 25.0 g (77%) white crystals, M.P. 123°–124° C. $^{13}$C-NMR (CDCl$_3$) delta=14.01 (CH$_3$); 63.0 (CH$_2$); 118.31 (CH); 162.95 (C=O).

b) Chelidamic acid-diamide

Chelidamic acid-diethylester (3 g, 0.013 mol) was dissolved in 45 ml of equal parts of methanol and concentrated aqueous ammonia and heated in a pressure bottle at 100° C. for 72 hours. The resulting solution was concentrated and recrystallized from dilute aqueous ammonia/methanol.

Yield: 1.3 g (58%), M.P. 330°–335° C. FAB-MS: 182 (m+1).

c) 2,6-Bis-aminocarbonyl-4-hydroxy-piperidine

A solution of chelidamic acid diamide (0.38 g/2.1 mmol) in absolute ethanol (100 ml) was hydrogenated at 65° C. under 3 atmospheres pressure hydrogen in the presence of 5% rhodium on carbon (0.22 g). After 17 hours, the catalyst was removed by filtration and the solvent was evaporated. The residue was dissolved in water (50 ml). The suspension was filtered and the filtrate was evaporated dryness to give the title compound. Yeild: 0.21 g (53.4%). The structure was confirmed by $^{13}$C-NMR (300 MHz, DMSO-d$_6$): 35.33, 55.58, 65.31, 166.57 ppm.

d) 2,6-Bis-aminomethyl-4-hydroxy-piperidine trihydrochloride 2,6-Bis-aminocarbonyl-4-hydroxy-piperidine (0.21 g/0.11 mmol) was dissolved in tetrahydrofuran (THF), and a solution of borane in THF (20 ml, 1M/20 mmol) was added. The mixture was refluxed overnight and methanol (5 ml) was then added at 0° C. The solvents were removed. Methanol (5 ml) was again added, and the solution was evaporated to near dryness. The residue was taken up in dry ethanol (20ml), saturated with HCl (g) and heated at reflux for two hours. The reaction mixture was concentrated and cooled to 0° C. The crystalline product was collected and dried under vacuum.

Yield: 0.21 g (71%) . MS (IP 70 eV, CI-NH$_3$): [M+i]=160.

(e) 2,6-Bis-aminomethyl-4-hydroxy-N,N',N''-pentakiscarboxymethyl-piperdine 2,6-Bis-aminomethyl-4-hydroxy-piperidine trihydrochloride (10mmol) is dissolved in water (10ml). The pH is adjusted to 10 with 4 M LiOH, and a solution of bromoacetic acid (55 mmol) and LiOH C55 mmol) in water (10 ml) is gradually added to the stirred mixture at ambient temperature. The temperature is gradually increased to 85 ° C. during 4 hours while the pH is kept in the alkaline range (8 to 10) with aqueous LiOH. The solution is allowed to cool to ambient temperature, neutralised with conc. hydrobromic acid, loaded on a strong cation exchanger (AG 5Wx4) and eluted with 6M aqueous ammonia. After evaporation down, the crude product is dissolved in water and lyophilised to yield the title compound.

EXAMPLE 2

3,5-Thiomorpholinodimethaneamine penta (acetic acid)

3 , 5-Thiomorpholinodimethaneamine ( 10 mmol) (as described by A. V. Eremev in Zh. Org . Khim 21 (1985) 2239) is dissolved in water (10 ml). The pH is adjusted to 10 with 4 M LiOH, and a solution bromoacetic acid (55 mmol) and LiOH (55 mmol) in water (10 ml) is gradually added to the stirred mixture at ambient temperature. The temperature is gradually increased to 85 ° C. during 4 hours while the pH is kept in the alkaline grane (8 to 10) with aqueous LiOH. The solution is allowed to cool to ambient temperature, neutralised with conc. hydrobromic acid, loaded on a strong cation exchanger (AG 5Wx4) and eluted with 6M aqueous ammonia. After evaporation down, the crude product is dissolved in water and lyophilised to yield the title compound.

EXAMPLE 3

2,6-Bis-aminomethyl-4-hydroxy-N,N',N''-petakiscarboxymethyl-piperidine a) 2,6-Bis-ethyloxycarbonyl-4-hydroxy-piperdine

The diester prepared as in Example 1a (20.0 g, 83.6 mmol) was dissolved in dry ethanol (200 ml). The solution was hydrogenated at 10 bar in the presence of rhodium on alumina (4.0 g) at 67° C. for 20 hours. After cooling, the solution was filtered and evaporated to give a yellow oil. The crude oil was purified by reverse phase chromatography to yield 10.8 g (53 %) of a yellow oil, FAB/MS: 246 (M+i). NMR confirmed the structure.

b) 2,6-Bis-aminocarbonyl-4-hydroxy-piperdine

The diester from Example 3a (9.9 g, 40.5 mmol) was dissolved in 140 ml 4M ammonia in dry ethanol and placed in an autoclave. After 2 days stirring at 100° C., the solution was cooled, the white precipitate was filtered off and washed with dry ethanol. Drying in vacuo yielded 5.6g (74%) of a white solid, mp. 252°–256° C., FAB/MS: 188 (M+I). NMR confirmed the structure.

c) 2,6-Bis-aminoraethyl-4-hydroxy-piperdine trihydrochloride

The diamide from Example 3b (5.5 g, 29.4 mmol) was suspended in 1 M borane in THF (590 ml) at 0° C. under nitrogen. After 1 hour with stirring, the colourless solution was refluxed overnight and cooled to ambient temperature. Methanol (590 ml) was added carefuly. The solution was evaporated to a clear oil and methanol (275 ml) and conc. HCl (11 ml) were added. After refluxing for 2 hours the solution was evaporated and the residue dissolved in 200 ml distilled water. The water phase was washed with 2×100 ml chloroform and evaporated to yield the title compound, 6.8 g (86%) white crystals, FAB MS: 160 (M+i), 268 (M 3HC1). NMR confirmed the structure.

d) 2,6-Bis-aminomethyl-4-hydroxy-N,N', N''-pentakiscarboxylmethy-piperdine

Alternative A:

The amine hydrochloride from Example 3c (5.0 g, 18.6 mmol) was suspended in dry acetone with dry potassium carbonate (30.9 g, 223 mmol) under nitrogen and stirred vigorously for 30 min. A solution of t-butyl bromoacetate (21.8 g, 111.7 mmol) in 20 ml acetone was added slowly, and the reaction was stirred overnight. Another 15 g of potassium carbonate was added and the reaction was refluxed for 3 hours. After cooling, the reaction was filtered and the filtrate evaporated to a brownish oil, which was chromatographed on silica to yield 8.5 g of a yellow oil, FAB/MS: 730 (M+1).

It was dissolved in 100 ml methylenechloride, and 100 ml trifluoroacetic acid was added slowly. After stirring for 3 hours, the solution was evaporated to an oil. This was stirred in ether for an ambient time and the solid filtered off and dried to yield 5.3 g (63 %) of a yellow solid, FAB/MS: 472 (M-Na)

Alternative B:

The amine hydrochloride from Example 3c (5.0 g, 18.6 mmol) was dissolved in water and the pH was adjusted to 9 with 4 M LiOH. Bromoacetic acid (16.5 g, 18.7 mmol) was carefully converted to the Li-salt with LiOH and added to the amine with stirring, the pH was kept between 9 and 10. After 3 hours the reaction was warmed to 80° C. for 5 hours, and then left stirring overnight at room temperature at pH 9.5. The reaction mixture was treated with a Dowex 50W X 4 ion exchanger in water for 2 hours. The resin was separated from the solvent, washed with water and treated with 25% ammonia in water for 1 hour. The resin was separated, and evaporation of the solution yielded 4.6 g (55%) yellow solid. FAB/MS: 450 (M+1).

EXAMPLE 4

2,6-Bis-aminomethyl-4-hydroxy-N,N', N'''-tris-carboxymethyl-N, N''-bis-methylaminocarbonylmethyl-piperdine The solid from Example 3d A (1.05 g, 2.2 mmol) was dissolved in dry pyridine (7.5 ml) under nitrogen and acetic anhydride (0.75 ml, 7.94 mmol) was added slowly. After 2.5 hours 30 ml of dry ether was added and the precipitate was separated by decantatation and washing with ether. The solid was added to 30 ml methylamine (40 %) in water and the reaction was stirred overnight. After evaporation the crude product was dissolved in 25 ml distilled water and the pH was adjusted to 3.0 with 1M HCl. Ethanolisopropanol in a 1:1 mix was added until precipitation was complete The solid was filtered off and dried to yield a yellow solid, 0.58 g (56 %). FAB/MS: 475 (M).

EXAMPLE 4.1

2,6-Bis-aminomethyl-4-hydroxy-N,N',N''-tris-carboxymethyl-N,N''-bis-dimethylaminocarbonylmethyl-piperdine The bis-dimethylamide was prepared analogously to the description in Example 4 by reacting the same amount of dimethylamine with the solid from Example 3d to yield 0.62g (56%). FAB/MS: 503 (M).

EXAMPLE 4.2

2,6-Bis-aminomethyl-4-hydroxy-N,N',N''-tris-carboxymethyl-N, N''-bis-(methyl-(2,3-dihydroxypropyl))-aminocarbonylmethyl-piperdine The bis-methylaminopropanediolamide was prepared analogously to the description in Example 4 by reacting the same amount, up to the point where the methylamine (40 %) in water was added. Methylaminopropandiol (2 equivalents) in 20 times the weight of the amine in dry dimethylacetamide was added under nitrogen and the reaction was stirred overnight at ambient temperature. Evaporation of solvent yielded a yellow oil, which was treated analogously to Example 4. F/LB/MS: 623 (M+1).

EXAMPLE 5

3,5-Bis--aminomethyl--N,N,N',N'',N''-pentakis-carboxymethylmorpholine a) 3-Carboxamido-5-cyano-4-benzylmorpholine

Benzylamine (19.3 g, 180 mmol) was dissolved in water (250 ml). The pH was adjusted to neutral by adding 6M HCl. Water (1500 ml) was added and the solution cooled on an ice/water mix. Sodium cyanide (17.6 g, 360 mmol) was dissolved in water (50 ml) and added to the solution. 2,2'-Oxybisacetaldehyde (18.4 g, 180 mmol) (prepared in accordance with J. Med. Chem. 27 638 (1984)) was dissolved in water (200 ml) and then added dropwise. The mixture was stirred for 1 hour at ambient temperature and left at 0° C. overnight. This gave a white precipitate which was filtered off and treated with THF (50 ml). The THF phase was cooled and the title compound was precipitated. Yield: 10.4 g (24 %). FAB/MS: 246 (M+1).

b) 3,5-Bis-aminomethyl-4-benzylmorpholine.

Lithium aluminium hydride (10 g, 264 mmol) was suspended in 200 ml dry THF and cooled to 0° C. under nitrogen. 3-Carboxamido-5-cyano-4-benzylmorpholine (4.3 g, 17.6 mmol), dissolved in dry THF (200 ml), was added dropwise. The mixture was refluxed for 48 hours, then cooled to 0° C. and water (10 g), 15% NaOH solution (10 g) and water (10 g) were added dropwise. The mixture was stirred for 30 min at ambient temperature, filtered and evaporated to dryness. 6 M HCl was then added and the mixture evaporated to dryness. The crude product was recrystallized from absolute ethanol and isolated as the hydrochloride salt. Yield: 3.6 g (59%). FAB/MS: 236 (M+1).

c) 3,5-Bis-aminomethyl-morpholine.

3,5-Bis-aminomethyl-4-benzylmorpholine (1.3 g, 5.5 mmol) was dissolved in methanol (50 ml). Ammoniumformiate (1.4 g, 22 mmol) and palladium on activated carbon (10 %, 5 g) were added. The reaction mixture was stirred at 50 ° C. under nitrogen for 3 hours. The catalyst was then filtered off and washed with several small portions of methanol and the solution evaporated to dryness. The tri-amine was used direcly in the next reaction step. FAB/MS: 146 (M+1).

d) 3,5-Bis-aminomethyl-N,N,N',N",N"-tert-butylpentakis-carboxymethyl-morpholine 3,5-Bis-aminomethyl-morpholine (0.36 g, 2.5 mmol) triethylamine (TEA) (2.53 g, 25 mmol) and tertbutyl bromoacetate (4.88 g, 25 mmol) were stirred at ambient temperature in dichloromethane overnight. The reaction mixture was diluted with chloroform and washed 3 times with water. The organic phase was dried (MgSO$_4$) and the title compound isolated after purification on a silica column; solvent ethylacetate. Yield: 0.90 g (50%). FAB/MS: 717 (M+1).

e) 3,5-Bis-aminomethyl-N,N,N',N", N"-pentakis-carboxymeehyl-morpholine

The tert-butyl protected pentaacid from Example 5d (1.0 g, 1.4 mmol) was dissolved in a mixture of TFA (10 ml) and dichloromethane (10 ml) and stirred at ambient temperature overnight. The solution was concentrated and treated with diethylether. The title product was isolated as a white product. Yield 0.87 g (80 %), FAB-MS: 436 (M+1).

EXAMPLE 6

3,5-Bis-aminomethyl-N,N', N"-tris-carboxymethyl-N,N"bis-methyl-carbamoyl-methyl-morpholine a) 3,5-Bis-[1'-(N-methyl-2,6-dioxomorpholine)]-morpholine-4-acetic acid The pentaacid from the example above (0.16 g, 0.36 mmol) was dissolved in pyridine (1.5 ml) and acetic acid anhydride {0.14 g, 1.39 mmol) was added. The mixture was stirred at ambient temperature for 2 hours and added to diethyl ether. The title product was isolated. Yield 0.10g (70%).

b) 3,5-Bis-aminomethyl-N,N',N"-tris-carboxymethyl-N,N"-bis (methyl-carbamoylmethyl)-morpholine 3,5-Bis-[1'-(N-methyl-2,6-dioxomorpholine)]-morpholine-4-acetic acid (0.10 g, 0.25 mmol) was added in portions to a solution of methylamine (40%) in water (10ml) at 0° C. The solution was stirred overnight at ambient temperature and the solvent was evaporated. Yield 0.112g (97%), FAB/MS: 462 (M+1).

EXAMPLE 6.1

3,5-Bis-aminomethyl-N,N', N"-tris-carboxymethyl-N,N"-bis-(N""-2,3-dihydroxy-propyl-N""-methycarbamoylmethyl)-morpholine 35-Bis-[1'-(N-methyl-2,6-dioxomorpholine)]-morpholine-4-acetic acid (0.28 g, 0.64 mmol) dissolved in DMA (2 ml), was added to a solution of N-methylaminopropane-2,3--diol (0.14 g, 1.3 mmol) in DMA (1.5 ml) at 0° C. under a nitrogen atmosphere. The solution was stirred overnight at ambient temperature and added to a mixture of diethyl ether and chloroform. The title product was isolated as a white solid. Yield 0.37 g (95%), FAB-MS: 611 (M+1).

EXAMPLE 6.2

3,5-Bis-aminomethyl-N,N',N"-tris-carboxymethyl-N,N"-bis-(N""-(5-hydroxy-3-oxa-pentyl)-N""-methyl-carbamoylmethyl)-morpholine 3,5-Bis-[1'- (N-methyl-2,6-dioxomorpholine)]--morpholine-4-acetic acid (0.30 g, 0.64 mmol) dissolved in DMA (1.5 ml) was added to a solution of 2'-methylamine-2-hydroxy-diethyl ether (prepared in accordance with J. Chem. Soc. London 532 (1947)) (0,038 g, 1.29 mmol) in DMA (0.5 ml) at 0° C. under a nitrogen atmosphere. The solution was stirred overnight at ambient temperature and added to a mixture of diethyl ether and chloroform. The title product was isolated as a white solid. Yield 0.38 g (93%), FAB -MS: 639 ( M+1).

EXAMPLE 7

2,5-Bis-aminomethyl-pentakis-carboxymethyl-3,4-dihydroxypyrrolidine a) 2,5-ethoxycarbonyl-3,4-dihydroxypyrrolidine 2,5-Bis-ethoxycarbonyl-3,4-bishydroxy pyrrol (1.0 g, 4.1 mmol) (prepared in accordance with Tetrahedron Letters 26 1839 (1985)) was dissolved in ethanolic H$_2$SO$_4$ (3 %) (50 ml). Rhodium on carbon (5%) (1.0 g) was added and the reduction reaction was allowed to run under hydrogen (9.4 bar) at 80° C. overnight. The catalyst was filtered off and the solvent evaporated. The reaction mixture was dissolved in water, the pH was adjusted with Na$_2$CO$_3$ and extracted with dichloromethane. The crude mixture was chromatographed on silica and the title product was isolated. Yield 0.1 g (10 %), FAB-MS: 248 (M+1).

b) 2,5-Biscarboxamide-3,4-dihydroxypyrrolidine 2,5-bis-ethoxycarbonyl-3,4-dihydroxypyrrolidine (0.19 g, 0.78 mmol) was dissolved in ethanol saturated with ammonia (60 ml) and heated in an autoclave at 80 ° C. for 24 hours. The suspension was allowed to cool to ambient temperature before the white crystalline product was filtered off, washed with ethanol and dried under vaccum. Yield: 0.07 g (50%), mp; 220–225 C. FAB/MS 190 (M+1)

c) 2,5-Bis-methaneamine--3,4-dihydroxypyrrolidinetrihydrochloride 2,5-Bis-carboxamide-3,4--dihydroxypyrrolidine (0.07 g, 0.37 mmol) was dissolved in a solution of borane in THF (40 ml, 1M). The mixture was refluxed overnight and methanol (45 ml) was then added at 0° C. The solvents were removed. Methanol (15 ml) was again added, and the solution was evaporated. The residue was dissolved in dry ethanol (50 ml), saturated with HCl fg) and heated under reflux for one hour. The suspension was allowed to cool to ambient temperature before the white crystalline product was filtered off, washed with ethanol and dried under vacuum. Yield: 0.07 g (70%), mp 230–240 C FAB-MS 162 (M+1-3 HCl)

d) 2,5-Bis-aminomethyl-pentakis-carboxymethyl-3,4-dihydroxypyrrolidine

The amine hydrochloride from Example 7c (0.70 g 0.26 mmol) was suspended in dry acetone with dry potassium carbonate (0.65 g, 4.68 mmol) under nitrogen and stirred vigorously for 30 min. A solution of t-butyl bromoacetate (0.61 g, 3.12 mmol) in 1.5 ml acetone was added slowly, and the reaction was stirred overnight at 50° C. After cooling, the reaction was filtered and the filtrate evaporated to a oil. Yield: 0.02 g. FAB/MS; 733 (M+1). The oil was dissolved in 0.5 ml methylenechloride and 0.5 ml trifluoroacetic acid was slowly added. After stirring for 2 hours, the solution was evaporated to dryness and the residue was suspended in diethyl ether. The white crystalline product was filtered off, washed with diethyl ether and dried under vacuum. Yield: 0.01g, FAB/MS: 452 (M+1).

EXAMPLE 8

2,3,5,6-Tetrakis-aminomethyl-deca-carboxymethyl-piperazine a) 2,3,5,6-Tetramethoxycarbonylpiperazine

A solution of tetrakis-methoxycarbonylpyrazine (5.3g, 16.9 mmol) (prepared in accordance with J. Org. Chem. 37 (19), p2963 (1972)) in 800 ml of dry ethanol, was hydrogenated at 50 bar in the presence of 10 g 5% palladium on charcoal at 80° C. for 16 hours. After cooling, the solution was filtered and evaporated to give slightly yellow crystals. Yield: 4.8 g (90%), mp. 162°–163° C. (Lit. 162°–163° C.). NMR confirmed the structure.

b) 2,3,5,6-Tetrakis-aminocarbonyl-piperazine

The tetraester from Example 8a (0.4 g, 1.3 mmol) was dissolved in dry methanol (50 ml), chilled with liquid nitrogen, and liquid ammonia (10 g, 590 mmol) was added. The mixture was stirred in a closed reactor at 50° C. for 2 days. Evaporation of the solvent left a white powder. Yield: 0,308 g (95%), m.p. 215°–220° C. (dec.) NMR and IR confirmed the structure.

c) 2,3,5,6-Tetrakis-aminomethyl-piperazine

Alternative A:

The tetraamide from Example 8b (0,258 g, 1 mmol) was suspended in 150 ml dry tetrahydrofurane. Freshly generated borane (from boron trifluoride etherate and sodium-borohydride) was bubbled slowly through the suspension with reflux under nitrogen. After the solution became clear (approx. 2 days) it was concentrated in vacuo and the residue hydrolyzed carefully. Water was distilled off in vacuo and the residue was stirred with concentrated hydrochloric acid (20 ml) at 100° C. for 30 minutes. The solution was concentrated to dryness and taken up with conc. sodium hydroxide solution (9ml) and concentrated again to dryness. The residue was extracted with chloroform (6×30ml), the extracts dried, filtered and concentrated to give 69mg (34%) of a yellow oil. FAB/MS: 203 (M+1).

Alternative B:

Pyrazinetetracarboxamide (2.58 g, 10 mmol) (prepared according to J. Org. Chem. 39 (9), p 1235 (1974)) was suspended in 500 ml dry tetrahydrofurane. Freshly generated borane (from boron trifluoride etherate and sodium borohydride) was slowly bubbled through the suspension with reflux under nitrogen. After the solution became clear (approx. 10 days) it was cooled and water added carefully. Concentrated hydrochloric acid was added and the mixture concentrated to dryness in vacuo. The residue was dissolved with 200 ml water, made alkaline (pH 12) by addition of sodium hydroxide pellets and the aqueous solution extracted continuously (3 days) with chloroform. The chloroform phase was concentrated and the residual oil distilled in vacuo (Kugelrohr) to give 1.42 g (65%) clear liquid b.p. 60°–80° C./0.004 mbar. FAB/MS: 219 (M+i) (Bis-boroamine compound). NMR and IR confirmed the structure. 0.3 g (14 mmol) of this oil is stirred with 5 ml concentrated hydrochloric acid for 12 hours at 100° C., concentrated in vacuo, dissolved in 5 ml water, made alkaline with sodium hydroxide pellets and the resulting slurry extracted with chloroform (6×10 ml). The dried (sodium sulphate) extracts were filtered and concentrated to yield 110 mg (40%) of a yellow oil.

d) 2,3,5,6-Tetrakis-decacarboxymethyl-aminomethyl-piperazine

The hexamine from Example 8c (0.2 g, 1 mmol) is suspended in dry acetone with dry potassium carbonate (1.65 g 12 mmol) under nitrogen and stirred vigorously for 30 min. A solution of t-butyl bromoacetate (1.17 g, 6 mmol) in 1 ml acetone is added slowly, and the reaction is stirred overnight. Another 0.8 g of potassium carbonate is added and the reaction refluxed for 3 hours. After cooling, the reaction is filtered and the filtrate evaporated to a brownish oil, which is purified by chromatography on silica. The oil is dissolved in 5 ml methylene chloride, and 5 ml trifluoroacetic acid is added slowly. After stirring for 2 hours, the solution is evaporated to dryness and the residue taken up in 5 ml 1M HCl. The water phase is washed with chloroform and evaporated to dryness.

EXAMPLE 9

2,5-Bis-aminomethyl-pentakis-carboxymethyl-3-hydroxypyrrolidine a) 2,5-Bis-ethoxycarbonyl-3-hydroxypyrrolidine 2,5-Bis-ethoxycarbonyl-3,4-dihydroxypyrrol (1.0 g, 4.1 mmol) was dissolved in ethanolic $H_2SO_4$ (3%) (50 ml). Rhodium on carbon (5 %) (1.0 g) was added and the reduction reaction was allowed to run under hydrogen (9.4 bar) at 80° C. overnight. The catalyst was filtered off and the solvent evaporated. The reaction mixture was dissolved in water, the pH was adjusted with $Na_2CO_3$, and extracted with dichloromethane. The crude mixture was chromatographed on silica and the title product was isolated. Yield: 0.2 g (21 %), FAB-MS: 232 (M+1).

b) 2,5-Bis-carboxamide-3-hydroxypyrrolidine 2,5-Bis-ethoxycarbonyl-3-hydroxypyrrolidine (0.02 g, 0.08 mmol) was dissolved in ethanol saturated with ammonia (30 ml) and heated in an autoclave at 80° C. for 24 hours before the solvent was evaporated. Yield : 0.01 g (53%). FAB-MS 174 (M+1).

c) 2,5-Bis-methaneamine-3-hydroxypyrrolidine-trihydrochloride 2,5-Bis-carboxamide-3-hydroxypyrrolidine (0.15 g, 0.37 mmol) was dissolved in a solution of borane in THF (40 ml, 1M). The mixture was refluxed overnight and methanol (35ml) was then added at 0° C. The solvents were removed. Methanol (15 ml) was again added, and the solution was evaporated. The residue was dissolved in dry ehanol (50 ml) , saturated with HCl (g) and heated under reflux for two hours. The suspension was allowed to cool at ambient temperature before the white crystalline product was filtered off, washed with ethanol, and dried under vacuum. Yield: 0.07 g (41%). FAB-MS 146 (M+1-3HCl).

d) 2,5-Bis-aminomethyl-pentakis-carboxymethyl-3-hydroxypyrrolidine

The amine hydrochloride from Example 9c (0.26 mmol) is suspended in dry acetone with dry potassium carbonate (4.68 mmol) under nitrogen and stirred vigorously for 30 min. A solution of t-butyl bromoacetate (3.12 mmol) in 1.5 ml acetone is added slowly, and the reaction is stirred overnight at 50° C. After cooling, the reaction is filtered and the filtrate evaporated to a oil. The oil is dissolved in 20 ml methylene chloride and 20 ml trifluoroacetic acid is slowly added. After stirring for 2 hours, the solution is evaporated to dryness and the residue is dissolved in 20 ml 1M HCl. The water phase is washed with chloroform and evaporated to dryness to yield the title compound.

EXAMPLE 10

Sodium salt of a gadolinium (III) chelate of 2,6-Bis-aminomethyl-4-hydroxy-N,N',N'''-pentakiscarboxymethyl-piperdine The penta acid from Example 3d A (1.0 g, 2.12 mmol) was dissolved in water, the pH was adjusted to 3.5 with 1 M NaOH and gadolinium oxide (0.67 g, 1.06 mmol) was added. The suspension was reacted for 24 hours under reflux, filtrated, and the filtrate evaporated to dryness to yield 1.2 g (95 %) of a yellow solid. FAB/MS: 625 (M+Na) .

EXAMPLE 11

Disodium salt of Dysprosium (III) chelate of 2,6-bis-aminomethyl-4-hydroxy-N,N',N'''-pentakis-carboxymethyl-piperidine The same amount of starting material was reacted with dysprosium oxide as described in Example 10. Yield: 1.3 g of a yellow solid (96%). FAB/MS: 653 (M+2Na).

EXAMPLE 12

Disodium salt of the qadolinium(III)chelate of 3,5-bis-aminomethyl-pentakis-carboxymethyl-morpholine 3,5-Bis-aminomethyl-morpholine-pentaacetic acid (0.20 g, 0.23 mmol) was dissolved in water (5 ml), the pH was adjusted to 5 with 1 M sodium hydroxide, and gadolinium(III) oxide (0,086 g, 0.23 mmol) was added. The suspension was stirred overnight at 90° C., filtered and precipitated with acetone, to give the title product. Yield 0. 255 g (94%) , FAB-MS 635 (M+1).

EXAMPLE 13

Gadolinium (III) chelate of 3,5-bis-aminomethyl-N,N', N'''-tris-carboxymethyl-N,N'''-bis-(methyl-carbamoyl-methyl)-mporphoine The bis-amide from Example 6b (0.09 g, 0.20 mmol) was dissolved in water (10 ml), the pH was adjusted to 5 with 1M sodium hydroxide, and gadolinium (III) oxide (0.036 g, 0.10 mmol) was added. The suspension was stirred overnight at 90° C., filtered and preciptiated with acetone, to give the title product. Yield 0.10 g (80%) , FAB-MS 617 (M+1).

EXAMPLE 14

Disodium salt of the dysprosium(III)chelate of 3 , 5-bis-aminomethyl-N,N,N',N'',N'''-pentakis-carboxymethyl-morpholine The penta acid from Example 5e (0.20 g, 0.23 mmol) was dissolved in water (5 ml), the pH was adjusted to 5 with 1 M sodium hydroxide and dysprosium (III) oxide (0,086g, 0.23 mmol) was added. The suspension was stirred overnight at 90° C., filtered and precipitated with acetone, to give the title product. Yield 0. 256 g (94%) , FAB-MS 641 (M+1).

EXAMPLE 15

Bismuth (III) chelate of 2,6-bis-aminomethyl-4-hydroxy -N,N',N'''-tris-carboxymethyl-N,N'''-bis-methylcarbamoyl-methyl-piperdine A neutral suspension of bismuth hydroxide is prepared by the neutralisation of a solution of bismuth chloride (0.12 g, 0.38 mmol, 4 ml) with sodium hydroxide, followed by centrifugation of the precipitate and resuspension of the precipitate in water (4 ml) . The suspension is added to a neutral solution of bis-amide (0. 176g 0.37 mmol) (Example 4) in water (4 ml) and the mixture is refluxed for 4 hours. The clear solution is evaporated , and the title compound is isolated as a white solid.

EXAMPLE 16

Preparation of a solution containing the pentasodium salt of 3,5-bis-aminomethyl-N,N,N',N'',N'''-pentakiscarboxymethyl-morpholine The penta acid from Example 5e (1.30 g, 3 mmol) was dissolved in water (15 ml) and the pH was adjusted to 7 by careful addition of 1 M sodium hydroxide. Water was added to 20 ml, the solution was filtered and then placed into a 20 ml vial. The vial was autoclaved.

The solution contained 0.15 mmol of the pentasodium salt of 3,5-bis-aminomethyl-N,N,N',N'',N'''-pentakiscarboxymethyl-morpholine per ml.

The solution is for the treatment of acute or chronic poisoning by heavy metals, such as lead.

EXAMPLE 17

Vial containing the technetium chelate of 3,5-bisaminomethyl N,N,N',N'',N''-pentakis-carboxymethyl-morpholine A vial is filled with 3,5-bis-aminomethyl-N,N,N',N'',N''-pentakis-carboxymethyl-morpholine from Example 5 (4 rag) and tin (II) chloride (0.22 rag) as dry powder.

A solution of 99mTc as pertecnetate in 0.9 % sterile sodium chloride should be added before use. The technetium chelate with 3,5-bis-aminomethyl-N,N,N',N'',N''-pentakis-carboxymethyl-morpholine is for the scintigraphic examination of organs such as brain and kidneys. The chelate is also useful for the studying of kidney function.

EXAMPLE 18

Preparation of a solution containing the salt of the zinc chelate of 2,6-bis-aminomethyl-N,N', N''-pentakis-carboxymethyl-4-hydroxy-piperidine The penta acid from Example 3d (0.90 g, 2 mmol) and zinc (II) carbonate (0.25 g, 2 mmol) were refluxed for 12 hours in water (15 ml). The mixture was cooled to ambient temperature, and the pH was adjusted to 6 by careful addition of 1 M sodium hydroxide. Water was added to give a volume of 20 ml, the solution was filtered and then placed into a 20 ml vial. The vial was autoclaved. The solution contained 0.1 mmol of the zinc chelate as trisodium salt per ml.

The solution may be used for treatment of acute or chronic poisoning by heavy metals, especially radioactive metals such as plutonium.

EXAMPLE 19

Preparation of a solution containing gadolinium (III) chelate of 2,6-bis-aminomethyl-4-hydroxy-N,N', N''-pentakis-carboxymethyl-piperdine Gadolinium(III) chelate of 2,6-bis-aminomethyl-4-hydroxy-N,N',N''-pentakis-carboxymethyl-piperidine (6.06 g , 10 mmol) (Example 10) was dissolved in 20 m of distilled water. The solution was filtered, placed in a 20 ml vial and autoclaved. The solution contained 0.5 mmol gadolinium per ml.

EXAMPLE 20

Preparation of a solution containing gadolinium (III) chelate of 2,6-bis-aminomethyl-4-hydroxy-N,N',N'',-tris-carboxymethyl-N,N''-bis-methyl-carbamoylmethyl-piperidine and 5 % of the sodium salt of the calcium chelate of 2,6-bis-aminomethyl-4-hydroxy-N,N', N'', tris-carboxymethyl-N,N''-bis-methyl-carbamoyl-piperidine 2,6-Bis-aminomethyl-4-hydroxy-N,N',N'',-tris-carboxymethyl-N,N''-bis-methyl-carbamoylmethyl-piperidine (0.22 g, 0.5 mmol) (Example 4) and calcium oxide 0.028 g, 0.5 mmol) were refluxed for 12 hours in water (10 ml). The mixture was cooled to ambient temperature and the pH was adjusted to 6.5 by careful addition of 1 M sodium hydroxide. The gadolinium (III) chelate of 2,6-bis-aminomethyl-4-hydroxy-N,N',N''-tris-carboxymethyl-N ,N''-bis-methyl-carbamoylmethylpiperidine (6.06 g, 10 mmol) was added, water was added to a total volume of 20 ml, the solution was filtered and placed into a 20 ml vial. The vial was autoclaved. The solution contained 0.5 mmol of the gadolinium(III) chelate of 2,6-bis-aminomethyl-4-hydroxy-N,N',N''-tris-carboxymethyl-N,N''-bis-methyl-carbamoylmethyl-piperidine per ml.

We claim:

1. A compound of formula I

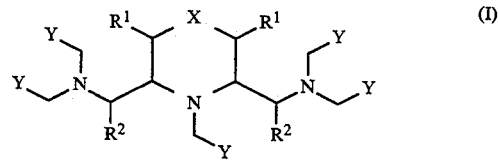

wherein X represents a bond, an oxygen or sulphur atom or a group of formula $CHR^1$ or $NR^3$;

each $R^1$ which may be same or different represents a hydrogen atom, a group of formula $OR^3$ or $NR^3R^3$ or a $C_{1-8}$alkyl or $(C_{1-8}$alkoxy)-$C_{1-8}$alkyl group optionally substituted by a hydroxyl group or by a group of formula $NR^3R^3$ or $CONR^3R^3$;

each $R^2$ which may be the same or different represents a hydrogen atom or a $C_{1-8}$alkyl or $C_{1-8}$alkoxy group optionally mono- or poly-substituted by hydroxyl or $C_{1-8}$alkoxy groups;

each $R^3$ which may be the same or different represents a hydrogen atom, an optionally mono-or poly-hydroxylated $C_{1-8}$alkyl group or a group of formula $CH_2Y$;

Y represents a group of formula COZ, CON(OH)$R^4$, POZ$_2$ or SO$_2$Z;

Z represents a group of formula $OR^4$, $NR^4R^4$, or

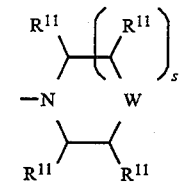

where each $R^{11}$ which may the same or different is a hydrogen atom, a hydroxyl group or an optionally hydroxylated $C_{1-8}$alkyl group, s is 0, 1 or 2, and W is a group $CHR^{11}$, $NR^{11}$ or an oxygen atom; and each $R^4$ which may bet he same or different represents a hydrogen atom or an optionally mono- or poly-hydroxylated $C_{1-8}$alkyl, $(C_{1-8})$alkoxy)-$C_{1-8}$alkyl or poly-($C_{1-8}$alkoxy)-$C_{1-8}$alkyl group; with the provisos that where is O then in the resultant 5 membered heterocyclic ring W is a $CHR^{11}$ group, and that where X represents a bond or a group $CHR^1$ at least one group $R^1$ or $R^2$ represents other than a hydrogen atom or an unsubstituted $C_{1-8}$-alkyl group, or a salt thereof.

2. A compound of formula I as claimed in claim 1 wherein Z represents a group of formula $OR^4$ or $NR^4_2$ and each $R^4$ which may be the same or different represents a hydrogen atom or an optionally hydroxylated alkyl group, or a salt thereof.

3. A compound of formula I as claimed in claim 1 wherein at least one group Z is of formula

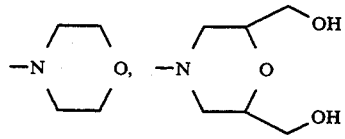

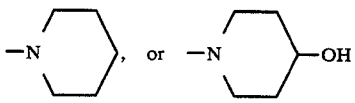

or a salt thereof.

4. A compound formula I as claimed in claim 1 wherein $R^1$ represents a hydrogen atom, a hydroxyl group or a hydroxylated alkyl group, $R^2$ represents a hydrogen atom or a hydroxylated alkyl group, $R^3$ represents a hydrogen atom or a group of formula $CH_2Y$, X represents a bond, an oxygen atom, an optionally hydroxylated methylene group or a group $NR^3$, Y represents a group of formula COZ and Z represents a hydroxyl group or a group $NHR^4$, where $R^4$ represents a hydrogen atom or an optionally hydroxylated alkyl group, or a salt thereof.

5. A compound as claimed in claim 1 having a formula:

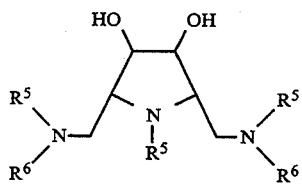
(Ia)

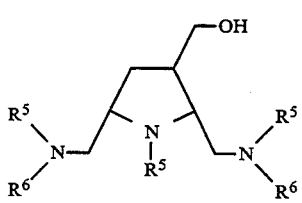
(Ib)

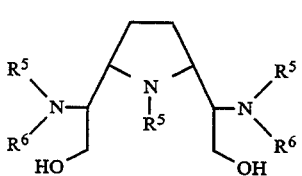
(Ic)

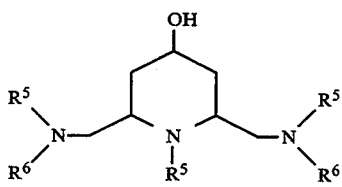
(Id)

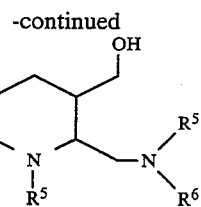
(Ie)

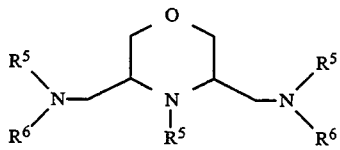
(If)

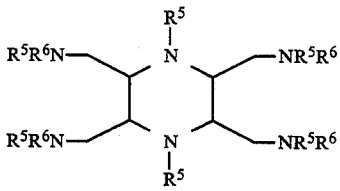
(Ig)

where $R^5$ represents $CH_2COOH$, $R^6$ represents $CH_2COOH$, $CH_2CON(CH_3)CH_2CHOHCH_2OH$, or $CH_2CONHR^7$ and $R^7$ represents a group

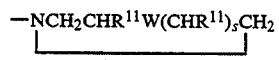

where W represents an oxygen atom or a group $CH_2$ or CHOH, s is 0 or 1 and $R^{11}$ is hydrogen, or where s is 1 and W is oxygen, each $R^{11}$ may also represent a $C_{1-4}$Hydroxylalkyl group,
or a slat thereof.

6. A compound as claimed in claim 1 wherein each Y group is a carboxyl group or a salt or amide thereof.

7. A process for the preparation of compounds as claimed in claim 1, said process comprising at least one of the following steps:

a) reacting a compound of formula II

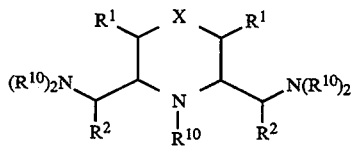
(II)

wherein X, $R^1$ and $R^2$ are as defined in claim 1 and $R^{10}$ represents a hydrogen atom or a group $CH_2Y$ where Y is as defined in claim 1, with the proviso that at least one hydrogen is nitrogen-attached, with a compound of formula III

L—$CH_2$—Y where L is a nucleophilic leaving group; and
b) converting a compound of formula I into a salt thereof.

8. A method of heavy metal detoxification practiced on the human or non-human animal body, said method comprising administering to said body a cheleting agent as claimed in claim 1 in the form of a salt with a physiologically a acceptable counterion.

* * * * *